(12) United States Patent
Klimenko et al.

(10) Patent No.: US 9,138,145 B2
(45) Date of Patent: Sep. 22, 2015

(54) INTEGRATION OF MRI INTO RADIATION THERAPY TREATMENT

(75) Inventors: Gordon Klimenko, Winnipeg (CA); Meir Dahan, Winnipeg (CA); Brendan Guyot, Winnipeg (CA); Victoria Hornblower, Winnipeg (CA); Labros Petropoulos, Winnipeg (CA); John Saunders, Winnipeg (CA); John Van Heteren, Foster City, CA (US); Jeff Winter, Winnipeg (CA); Hongxiang Yi, Winnipeg (CA)

(73) Assignee: Imris Inc., Winnipeg, MB (CA)

( * ) Notice: Subject to any disclaimer, the term of this patent is extended or adjusted under 35 U.S.C. 154(b) by 266 days.

(21) Appl. No.: 13/523,257

(22) Filed: Jun. 14, 2012
(Under 37 CFR 1.47)

(65) Prior Publication Data
US 2013/0317343 A1 Nov. 28, 2013

Related U.S. Application Data

(60) Provisional application No. 61/497,236, filed on Jun. 15, 2011.

(51) Int. Cl.
*A61B 5/05* (2006.01)
*A61B 5/00* (2006.01)
*A61B 5/055* (2006.01)
(Continued)

(52) U.S. Cl.
CPC .............. *A61B 5/0046* (2013.01); *A61B 5/055* (2013.01); *A61B 5/0555* (2013.01); *A61B 5/4836* (2013.01); *A61N 5/1001* (2013.01); *A61N 5/1039* (2013.01); *A61N 5/1077* (2013.01); *G01R 33/4808* (2013.01);
(Continued)

(58) Field of Classification Search
USPC .................. 600/407, 409–411; 324/306–308
See application file for complete search history.

(56) References Cited

U.S. PATENT DOCUMENTS

| | | |
|---|---|---|
| 3,720,817 A | 3/1973 | Dinwiddie |
| 5,402,783 A | 4/1995 | Friedman |

(Continued)

FOREIGN PATENT DOCUMENTS

| | | |
|---|---|---|
| WO | WO/03/008986 | 1/2003 |
| WO | WO/2009/155700 | 12/2009 |
| WO | WO/2010/111772 | 10/2010 |

OTHER PUBLICATIONS

Hoult D I et al: "The Engineering of an interventional MRI with a movable 1.5 Tesla magnet", Journal of Magnetic Resonance Imaging, Society for Magnetic Resonance Imaging, Oak Brook, IL, US, vol. 13, No. 1, Jan. 1, 2001, pp. 78-86.

(Continued)

*Primary Examiner* — Joel F Brutus
(74) *Attorney, Agent, or Firm* — Adrian D. Battison; Ade & Company Inc.

(57) ABSTRACT

Apparatus for radiation therapy combines a patient table, an MRI and a radiation treatment apparatus mounted in a common treatment room with the MR magnet movable from a position outside a radiation shielded door to an imaging position. An RF-shielded door is movable between a position, separating part of the treatment apparatus from the magnet and an open position allowing access of the patient to the treatment apparatus. In one configuration there is a row of treatment rooms and the magnet is mounted to move along a passageway outside the row of radiation shielded doors of the rooms.

15 Claims, 9 Drawing Sheets

(51) Int. Cl.
   *G01R 33/48* (2006.01)
   *A61N 5/10* (2006.01)
(52) U.S. Cl.
   CPC .......... *A61N 2005/1055* (2013.01); *A61N 2005/1063* (2013.01); *A61N 2005/1094* (2013.01)

(56) References Cited

U.S. PATENT DOCUMENTS

| | | | |
|---|---|---|---|
| 5,432,544 A * | 7/1995 | Ziarati | 600/410 |
| 5,537,452 A | 7/1996 | Shepherd et al. | |
| 5,778,047 A | 7/1998 | Mansfield | |
| 5,851,182 A * | 12/1998 | Sahadevan | 600/407 |
| 6,198,957 B1 | 3/2001 | Green | |
| 6,366,798 B2 | 4/2002 | Green | |
| 6,419,680 B1 | 7/2002 | Cosman | |
| 6,725,078 B2 | 4/2004 | Bucholz | |
| 6,862,469 B2 | 3/2005 | Bucholz et al. | |
| 7,758,241 B2 | 7/2010 | Sliski et al. | |
| 2005/0197564 A1 | 9/2005 | Dempsey | |
| 2007/0055090 A1 * | 3/2007 | Neustadter et al. | 600/3 |
| 2009/0030305 A1 * | 1/2009 | Hoogeveen | 600/422 |
| 2009/0306494 A1 * | 12/2009 | Scarth et al. | 600/411 |

OTHER PUBLICATIONS

Karlsson M et al: "Dedicated Magnetic Resonance Imaging in the Radiotherapy Clinic", International Journal of Radiation: Oncology Biology Physics, Pergamon Press, USA, vol. 74, No. 2, Jun. 1, 2009, pp. 644-651.

Raaymakers B W et al: "Note; Integrating a 1.5 T Mri scanner with a 6 MV accelerator: proof of concept: Proof of concept MRI accelerator", Physics in Medicine and Biology, Taylor and Francis ltd. London, GB, vol. 54, No. 12, Jun. 21, 2009, pp. N229-N237.

M Barkati et al: "The use of Magnetic resonance imaging for image-guided brachytherapy", Journal of Medical Imaging and Radiation Oncology, vol. 54, No. 2, Apr. 1, 2010, pp. 137-141.

\* cited by examiner

INTEGRATION OF MRI INTO RADIATION THERAPY TREATMENT

This application claims the benefit under 35 USC 119(e) from Provisional Application 61/497,236 filed Jun. 15, 2011.

This invention relates to a system to integrate of MRI into radiation therapy treatment. The treatment using radiation can be conventional targeted beam therapy or brachytherapy where radiating material is introduced into the body of the patient.

BACKGROUND OF THE INVENTION

External beam radiotherapy (RT) devices generally include a linear electron beam accelerator which is mounted on a gantry, which can rotate about an axis approximately parallel to the patient lying on the patient couch. The patient is treated using either an electron beam or an X-Ray beam produced from the original electron beam. The electron or X-Ray beam is focused at a target by the combination of the use of a collimator and the rotation of the beam. The patient is placed on a couch that can be positioned such that the target lesion can be located in the plane of the radiation beam as the gantry rotates.

The objective of the radiation therapy is to target the lesion with a high dose of radiation with minimal impact on all the surrounding normal tissue. An initial treatment planning procedure is performed prior to external beam RT delivery to localize the tumour and other critical structures surrounding the tumour. This planning procedure typically involves CT imaging to identify these structures. Based on the segmented tumour and surrounding tissue structures, a set of beam orientations and collimator settings are developed through an iterative process to determine the optimal dose distribution pattern that maximizes dose to the tumour whilst minimizing dose to surrounding critical avoidance structures.

MRI is currently the optimal modality for tumour localization based on the higher soft-tissue contrast, compared with CT, and can be incorporated into the treatment planning workflow. Although MRI provides good location of the tumour for treatment planning purposes, these treatment planning images are normally collected several days prior to treatment, and, as such, may not be completely representative of tumour location on the day of treatment. To address this limitation, oncologists tend to increase the target volume ensure all the tumor tissue receives the maximum dose. The expectation is that all cells in the targeted region will receive the required RT treatment dose, and that this increased treatment target volume will lessen the impact of errors between treatment planning dose distribution, and the dose delivered to the actual region of the lesion. However, this increased treatment margin also produces collateral tissue damage that may have a significant impact of the quality of life of the patient and increase the possibility of secondary RT-induced cancer.

To mitigate the need for increased treatment margins, clinicians have employed a method referred to as image-guided external beam radiation therapy, in which an image is acquired immediately prior to RT treatment delivery. One such available solution involves completely integrating the MRI system with a linear accelerator to enable real-time imaging of the tumour during RT treatment. However, this design is complex, expensive and may involve serious compromises on the functional performance of both the MRI and linear accelerator.

The treatment planning images are typically collected days prior to the actual fractionated treatment delivery that can occur over the course of several weeks. As such, the position of the tumour in the treatment imaging plans may not be representative of the actual lesion position on each day of treatment. By incorporating image guidance immediately before each treatment session, it is possible to determine the exact position of the lesion within each treatment session. Acquiring MR images immediately before RT treatment would identify the exact lesion location, and define the correct gantry positions for conformal radiation delivery.

To integrate pre-treatment MR images into the RT treatment workflow requires a mapping of the MRI coordinate space to the RT system coordinate space, to ensure correct alignment of the linear accelerator gantry for treatment. The RT system coordinate space is defined by the gantry/room mounted x-ray/cone beam CT (CBCT) system that is typically used in conventional image guided-radiation therapy. One solution would involve registering the pre-treatment MRI and x-ray images to determine the relative coordinate transformation required to align "MRI space" and "RT space", using manual registration of fiducial markers on the surface, or inserted into, the patient. Typically this involves an operator identifying multiple control points in the MRI space and also identifying the same representative points in the RT unit's X-ray images. Although simplistic, this is a manual, time-consuming, and error-prone technique. Moreover, it is possible that the fiducial markers might move, particularly if affixed to the skin of the patient. Alternatively, patient registration can be performed using an image-based anatomical registration method that maps the two coordinates systems using specific anatomical features. This alternative method is based solely on patient anatomy and involves registering two image datasets with considerably different image contrasts, and is prone to registration errors.

A radiotherapy device generally includes a linear electron beam accelerator which is mounted on a gantry and which can rotate about an axis which is approximately parallel to the patient lying on the patient couch. The patient is treated using either an electron, γ- or X-Ray beam produced from the original electron beam. The beam is focused at a target by the combination of the use of a collimator and the rotation of the beam. The patient is placed on a couch which can be positioned such that the target lesion can be located in the plane of the electron beam as the gantry rotates. This patient couch is designed to adjust the position of the patient to align the targeting exactly at the isocentre of the RT system using up to six degrees of motion (x, y, z, roll, pitch, and yaw). The current couch designs employed by several manufacturers employ a cantilevered couchtop that enables a sufficient range of motion to treat disease sites throughout the entire body.

Bucholz et al. discloses a method to combine proton beam therapy with an MRI system in U.S. Pat. No. 6,862,469. This method only discusses proton therapy, describes a stationary MRI, in which the beam is sent through a gap in the magnet. This application suggests mat shielding methods can be used to remove magnetic and RF interference, although this is only briefly mentioned.

Dempsey discloses a method to deliver RT using cobalt-60 as the source of ionizing radiation with a stationary open MRI system in U.S. Patent Application Publication No. 2005/0197564 device and a process for performing high temporal- and spatial-resolution MR imaging of the anatomy of a patient during intensity modulated radiation therapy (IMRT) to directly measure and control the highly conformal ionizing radiation dose delivered to the patient for the treatment of diseases caused by proliferative tissue disorders. This invention combines the technologies of open MRI, multileaf-collimator or compensating filter-based IMRT delivery, and cobalt teletherapy into a single co-registered and gantry mounted system.

Carlone discloses a method to combine MRI and a radiation therapy system in WO/2009/155700, entitled Radiation Therapy system. This method was developed in Alberta and describes an approach that exposes the linear accelerator to the magnetic field, and uses the magnet forces to direct the particles along the central axis.

Lagendijk discloses a method to combine MRI and radiation therapy using a global coordinate system in WO/2003/008986, entitled MRI in guided radiotherapy and position verification. In this system the MRI is actively shielded to prevent the static magnetic fields from interfering with the linear accelerator operation.

Orbital Therapy discloses in U.S. Pat. No. 7,758,241 a self-shielded radiotherapy device, that does not require a traditional bunker for operation.

Other patents describing prior art include:
U.S. Pat. No. 6,198,957—Radiotherapy Machine including Magnetic Resonance imaging system
U.S. Pat. No. 6,366,798—Radiotherapy machine including Magnetic Resonance Imaging system.
U.S. Pat. No. 6,725,078—System combining proton beam irradiation and magnetic resonance imaging.
U.S. Pat. No. 5,402,783—Method of Minimizing distortion to radiation isodose.
U.S. Pat. No. 6,419,680—CT and MRI visible index markers for stereotactic localization. In this patent application, the inventors claim that skin-based localizer markers can be used for stereotactic localization in both MRI and CT.
WO 03/008986 A2 MRI in guided radiotherapy and position verification Submitted by Utrecht, this patent describes incorporating an independent world coordinate isocentre calibration system consisting of fiducial table MR-markers and an independent table position verification system.
IMRIS also has also filed PCT Application PCT/CA2010/000422 filed Mar. 29, 2010 published 7 Oct. 2010 under publication no. WO 2010/111772 for a patient support system for integrating X-ray imaging with MR, in Support Component for Use in Imaging by Magnetic Resonance and X-ray. This application describes a support structure that is both MR compatible and radiolucent.
In U.S. Pat. No. 5,778,047 (Mansfield) issued Jul. 7, 1998 Varian discloses patient couch-top in entitled Radiotherapy Couch Top; however, materials in the design include carbon fiber, and therefore not MR compatible. The design includes bearings for longitudinal motion that enables panels in the couch top to be inserted and removed.
In U.S. Pat. No. 3,720,817 (Dinwiddie) issued Mar. 13, 1973 Varian also has a patent on the overall RT system, entitled Automated Radiation Therapy Machine. In this patent, the patient couch is identified and described.

The disclosure of all of the above cited references is hereby incorporated herein by reference or may be referred to for further details of components and methods not specifically set out herein.

SUMMARY OF THE INVENTION

According to the invention there is provided an apparatus for radiation therapy of a patient comprising:
a patient support table;
a magnetic resonance imaging system for acquiring MR images of an imaging volume including the target location of the patient;
the imaging system including:
an MR magnet operable to generate a magnetic field to be applied to the patient, the magnet having a cylindrical bore for surrounding the target location of the patient;
an RF transmit coil arrangement for generating an RF pulse in a transmit stage to be applied to the subject to be imaged such that the subject generates an MR signal in response to the magnetic field and the RF pulse applied;
a receive coil arrangement for acquiring the MR signal in a receive stage;
and a signal processing system for receiving the MR signal for carrying out signal processing by which an image is generated;
a treatment apparatus for applying a radiation therapy to a target location in the patient on the support table;
the patient support table and the treatment apparatus being mounted in a treatment room which is radiation shielded and has an opening which includes a radiation shielded door arrangement operable to close the opening;
the MR magnet being mounted for movement from a position exterior of the radiation shielded door arrangement into the opening to an imaging position for cooperation with the patient on the patient support table for MR imaging;
the MR magnet being mounted for movement from the imaging position to the exterior position for the radiation treatment of the patient on the patient support table;
wherein there is provided an arrangement for preventing RF signals from the treatment apparatus from interfering with the MR imaging system during imaging at the patient support table;
and wherein both the patient support table and the treatment apparatus are arranged to remain at a treatment location in the treatment room when the magnet is moved to the imaging position.

Preferably the arrangement for preventing RF signals from interfering with the imaging comprises an RF-shielded door arrangement in the treatment room arranged to be movable between a closed position, separating at least part of the treatment apparatus from the magnet when in the imaging position, and an open position in which the treatment apparatus is accessible to the patient on the patient support table for radiation therapy, the RF-shielded door arrangement being arranged in the closed position to isolate RF noise critical electronic components of the treatment apparatus from the magnet and receive coil arrangement while allowing the critical electronic components to remain active without shutdown.

Preferably the patient support table comprises a patient support couch cantilevered on a support base which includes a turntable formed of a conductive material for rotation about a vertical axis and wherein the RF-shielded door arrangement includes at least a part which extends across the turntable so as to exclude the part of the turntable from the MR magnet.

Preferably the part of the RF shielded door arrangement extends across the turntable at an angle inclined to a longitudinal axis of the bore of the magnet.

Preferably the RF shielded door arrangement includes a portion arranged on each side of the treatment apparatus at right angles to the longitudinal axis.

Preferably the RF-shielded door arrangement includes a first part extending partly across the turntable and a second part extending partly across the turntable where the parts meet at an apex to enclose the treatment apparatus.

Preferably the RF-shielded door arrangement includes a part extending fully across the turntable to a position on either side of the turntable where the treatment apparatus includes a head rotatable about an axis longitudinal of the treatment room and wherein the head is turned to a position at one side of the patient support table to enable the part to pass across the turntable with the head on a side of the part remote from the magnet.

Preferably cables for providing control signals to the patient support table pass through an RF shield and include an RF filter.

Preferably the patient support table includes control elements operated by fiber optic cables which pass through an RF shield.

Preferably there are provided at least three rooms in a row including said Radiation treatment room which is used for external beam treatment, a third room for a brachytherapy system spaced from the Radiation treatment room and a second diagnostic room intermediate the treatment room and the third room with the magnet being movable into each of the rooms to provide image-guidance for both the external beam and brachytherapy RT procedures using the same movable MRI magnet.

Preferably there are provided at least three rooms in a row at least one of which comprises said Radiation treatment room and wherein the magnet is arranged to move linearly along a path outside the row of rooms and to rotate at each room to cooperate with a patient support table therein.

Preferably the patient support table is arranged to rotate 180 degrees from the isocenter of the treatment apparatus for cooperation with the MR magnet in MR imaging procedures, and then rotate back to the isocenter for treatment.

Preferably the patient support table employs several electronic motors designed to provide different degrees of motion with the motors and controls therefor arranged to avoid interaction of the MRI static magnetic field.

Preferably there is provided an automated safety system which de-energizes motors of the patient support table when the patient support table is locked in place for MR imaging, and prevents any unsafe actions once locked into place.

Preferably the safety system also guarantees that the patient support table is in the appropriate locked position prior to the magnet moving over the patient.

One concept disclosed herein is the ability to perform MR imaging in the same room as external RT without RF interference from the RT system using a specific placement of RF-shielded doors between the two systems that open and close in between radiation therapy and MR imaging. This provides an arrangement aimed to directly combine MR with RT in a hybrid suite. Furthermore, this arrangement can also provide the necessary room configuration requirements to perform brachytherapy procedures.

The arrangement described provides a movable MRI system that can be brought into the room to image the patient before treatment, and then retract the MRI system immediately prior to RT treatment. To implement this movable MRI system with external beam RT treatment requires a novel room configuration and specific shielding requirements to minimize the effects of the linear accelerator on MR image quality, and to ensure optimal operational characteristic of the linear accelerator.

As MR image formation is based on radiofrequency transmission (RF) and detection. MRI systems are typically enclosed within a RF-shielded room to prevent spurious RF signals, external to the MRI system, from interfering with the image acquisition. Depending on the sequence employed, external RF signals create unacceptable artifacts in the image that hinder diagnosis, and degrade the overall image quality. Any electronic devices in the RE-shielded room may be sources of RF, and interfere with image acquisition. Therefore, to combine MRI with RT requires that all devices within the RF-shielded room are RF quiet, i.e., do not generate detectable RE noise. In standard linear accelerators, a number of electronic devices exist that may generate RF noise. One solution to this problem of RF noise involves shutting off all electronic devices in the RT unit during MR imaging, and subsequently powering these devices on for RT treatment. However, this solution has several drawbacks. Thus critical components in the linear accelerator as well as onboard X-ray imaging systems require significant 'warm up' time. Accuracy of the RT system may be compromised by shorter 'warm up' times. Patient throughput is reduced. Repeated power cycling of the electronic components may reduce the overall lifetime of the system. Power up/power down may require additional calibration steps to ensure safe and accurate operation of the device. A better solution involves isolating the critical electronic components of the RT system from the MRI using a set of RF-shield doors between the MRI and RT system that are closed during MR imaging, and opened for radiation treatment.

Beyond external beam radiation therapy, which involves radiation delivery via linear accelerator, brachytherapy has also been demonstrated as a useful alternative for treating certain cancerous tumours, primarily tumours in the cervix and prostate. Unlike external beam RT, brachytherapy targets the tumour from within using selected radioactive isotopes that generate radiation dose deposition based on the γ-ray or X-ray energy levels emitted from the source isotope. The advantage of brachytherapy is that the radiation dose is localized to the tumour itself, with minimal impact on the surrounding tissue.

Briefly, the brachytherapy workflow involves inserting either high or low dose radioactive seeds directly into the tumour through a set of catheters. The position of each seed is based on a prescribed dose distribution pattern generated during treatment planning. Similar to external beam therapy, brachytherapy procedures benefits from integration of MR imaging procedures immediately prior to treatment delivery. Moreover, ability to image the catheter positions after insertion into the tumour improves the reliability of dose delivery to the tumour during the seed insertion procedure. One possible solution involves conducting the MRI procedures a standard diagnostic room and then transporting the patient to a brachytherapy bunker for catheter placement and treatment delivery. This approach is problematic, because the patient moves in transit, such that the images are no longer representative of the current tumour position. A better solution involves integrating brachytherapy procedures with a movable MRI system that is moved into the brachytherapy bunker for imaging, and then retracted for catheter positioning and treatment delivery. Current brachytherapy procedures require equipment, such as portable ultrasound/x-ray image guidance systems and a portable 'afterloader' that delivers the radioactive seeds through the catheters, which generate significant RE noise. Therefore, this solution requires a unique room configuration to provide radiation and RF-shielding for the MRI during brachytherapy catheter insertion and radioactive seed delivery.

The external beam and brachytherapy solutions can be combined with a diagnostic room in the middle to provide a comprehensive three-room solution that provides image-guidance for both external beam and brachytherapy RT procedures using the same movable MRI system.

In one design, the MR-guided external RT system involves two separate rooms; the first is a radiation-shielded "bunker" that houses the RT system (linear accelerator); and, the second room houses the MRI for basic diagnostic procedures.

The MRI moves into the RT bunker to acquire images of the patient, and then returns to the diagnostic room prior to radiation treatment.

The arrangement described provides a room configuration and two sets of doors to enable the movable IMRIS MRI system to be incorporated with a radiation therapy (RT) system without inference between the two systems. One set of RF- and radiation-shielded doors are placed between the RT system and the diagnostic room, which is closed during RT procedures to minimize radiation exposure to subjects within the diagnostic room, and to ensure that the RF noise from the RT system components do not interfere with imaging studies performed in the diagnostic room during treatment. A novel second set of RF-only-shielded doors are located within the RT bunker room, situated between the RT system and the MRI (in the pre-RT imaging position). This unique set of RF-shielded doors, when closed, isolates the critical electronic components of the RT system from the MRI to prevent spurious RF noise from interfering with the MR image acquisition.

The basic workflow for this invention for external beam RT is as follows:

Patient couch is rotated 180 degrees from the external beam RT system isocenter, and locked into place, External beam RT bunker doors open and movable magnet moves over the patient, RF shielding doors between the MRI and RT system close, Patient is imaged with the MRI system, MRI system is moved back to the diagnostic room, and external beam RT bunker doors close, RF shielding doors are opened and the patient couch is rotated 180 degrees back to the isocenter of the external beam RT system, and then Conformal radiation treatment is delivered.

The RF-shielding doors are located between the MR and RT systems, with doors that span the bunker room at approximately a 45 degree angle relative to the patient. The door orientation and position of the doors within the room will be maintained for each site, however, differences in the linac vault widths will be accounted for with a RF-shield wall on each side of the doors perpendicular to the patient.

The arrangement described provides safety control systems integrated into the patient couch to prevent movement when in position for MR imaging to mitigate the possibility of collision between the patient couch and RF shielded doors. Moreover, detectors on the RF doors prevent the doors from closing if there is an object within the path of movement.

This room configuration includes either a separate access to the RT area within the RF-shielded doors, or a separate manual override to enable egress for a person trapped behind the RF-shielded doors via a manual override switch that allows someone the ability to open the doors manually. This manual override system functions even in the event of a complete power failure.

A second suite configuration involves three separate rooms: an external beam RT bunker room, a diagnostic imaging room and a brachytherapy bunker room. In this three-room suite configuration, the external beam RT bunker room and diagnostic imaging room are as described above. The additional brachytherapy room in the three-room suite is a radiation and RF shielded bunker room with a patient table which is basically held at a stationary position with the necessary adjustments for movement as required for imaging and treatment. However the table can also be mounted for movement away from the stationary position. The MRI system moves into the brachytherapy room to perform imaging procedures, and then retracts for the insertion of the catheters and delivery of the radioactive isotope seeds. In this invention, a set of RF and radiation shielded doors is located between the brachytherapy bunker and the MRI diagnostic room. This set of doors is opened to allow the MR system to enter the brachytherapy room, and is closed after the MRI has moved back into the brachytherapy room. The brachytherapy bunker doors minimize radiation exposure from brachytherapy procedures for subjects in the diagnostic imaging room, as well as eliminate RF noise effects on MR image quality caused by equipment used in brachytherapy catheter insertion or seed delivery (i.e., portable x-ray or ultrasound system).

The basic workflow for the brachytherapy component of this invention is as follows:

Patient lies on brachytherapy table in treatment position,

Brachytherapy bunker doors open and movable magnet moves over the patient,

Patient is imaged with the MRI system,

MRI system is moved back to the diagnostic room, and brachytherapy bunker doors close, Catheters for the brachytherapy seed delivery are inserted, Brachytherapy bunker doors open and movable magnet moves over the patient, Patient is imaged with the MRI system with the MRI visible catheters inserted into treatment position, MRI system is moved back to the diagnostic room, and brachytherapy bunker doors close, Brachytherapy seeds are inserted through the catheters into the tumour for conformal treatment delivery.

The two major invention concepts, for external beam and brachytherapy pre-treatment imaging with a movable MRI system can be combined in several configurations:

Two Room:
a) external-beam RT bunker+diagnostic room,
b) external-beam RT bunker+brachytherapy bunker,
c) brachytherapy room+diagnostic room.

Three Room:
d) external-beam RT bunker+diagnostic room+brachytherapy bunker,
e) external-beam RT bunker+diagnostic room+external-beam RT bunker,
f) brachytherapy bunker+diagnostic room+brachytherapy bunker.

In addition, where it is required to provide registration between the MR images and the RT images generated for the treatment, many different registration systems can be used. One approach for registration is a system where fixed markers are used to automatically map the MR and RT coordinate systems (using the onboard X-ray component of the RT system), which is independent of patient anatomy. These markers are in one embodiment mounted into the patient table, and surrounding patient immobilization devices, and provide a consistent and rigid "global" frame of reference to map between the two coordinate systems.

An array of fiducial markers is embedded into a RT treatment couch top, which is also utilized for pre-treatment MRI acquisition. With this arrangement, the markers will be located beneath the patient so as not interfere with the patient position and immobilization. Embedding the markers in the couch top will also circumvent the need to affix markers to the surface of the patient and will provide a rigid and consistent 'global' reference frame for both MRI and RT imaging acquisitions.

To facilitate registration of the MRI and RT image coordinate systems, the fiducial markers can be both MR and X-ray visible and arranged within the field-of-view for both systems. The markers will be arranged in a series of unique "fiducial frames" that are embedded into the patient couch top using special shapes and geometries designed to provide high registration accuracy. A series of different anatomic-based fiducial frames will be assigned a particular position in the patient couch top along the inferior/superior (i.e., head-to-toe) direction. Accuracy of the fiducial markers is related to the distance between the fiducial frame and the tissue region of treatment. As such, each of the fiducial frames will be specifically designed for the primary anatomical areas typically targeted in RT treatment, e.g., 1. head/neck, 2. lung, 3. abdominal, and 4. pelvic. Each fiducial frame will consist of several markers in a unique geometry and arrangement that will create a 'signature' for the automatic registration software to identify each frame independently. The MR/X-ray markers can encode the position of the fiducial frame used for each anatomic treatment area, allowing automatic identification of more than one frame with its associated geometry. Markers geometry may also be designed such that if only a subset of the MR/X-ray markers can be identified in the MR and RT imaging system fields-of-view, their location on the frame can still be uniquely identified.

In one embodiment, a bunker is used to contain the RT system on one side, while on the other side of the room is a bunker door that can open, and allow the movable MRI to enter the room. First, the patient will be positioned on the patient couch and rotated 180 degrees away from the RT system isocentre. The MRI system moves into the room, and acquire images with the patient in the imaging position, with the fiducial markers embedded into the patient couch top as described above. Once imaging is complete, the movable MRI leaves the room, and the patient is back to the RT system isocentre for X-ray imaging and treatment. In this configuration, the patient position is consistent between both the RT and MRI positions, ensuring that the global fiducial frame is representative of the patient position in both orientations.

A computer algorithm provides an automatic approach to identify each fiducial frame based on the unique marker positions, and to calculate the exact location of the marker frame in three-dimensional space. This fiducial frame represents a "global" coordinate system for registration purposes. The couch-top fiducials are first identified in pre-treatment MR images to establish the global coordinate system. In the next step, the same couch-top is moved to the RT system imaging position, and CBCT, 2D X-ray, or X-ray fluoroscopic images are obtained, in which the same fiducial markers are detected. The automatic computer algorithm registers the global fiducial reference frame between the two imaging modalities and calculates the coordinate mapping between the MRI space and RT space. This allows automatic registration of the MR and RT coordinate systems, without user interaction. However, the software workflow provides a display of the registered MRI and x-ray images for visual confirmation of the alignment of the markers, as well as the alignment of the major anatomical structures. The clinical staff are able to confirm the success of the automatic registration prior to treatment. The coordinate system transformation matrix can then be used in the RT system to align the gantry isocentre with the pre-treatment MRI position verification, and start treatment.

This arrangement provides the ability to automatically produce the coordinate mapping from a set of MR images to the RT system coordinate system.

Specific advantages may include:
Enhanced workflow by automating the image registration,
Fiducial frame is semi-permanently embedded into the patient couch and remain in place indefinitely (markers do not need to be removed),
Placement of fiducials in the couch-top ensures a consistent and rigid frame of reference,
Effectiveness of the fiducial frame not affected by draping, or any other immobilization devices,
Since the markers are independent of any MR coil and patient anatomy, they are not dependent on coil placement, coil movement or patient positioning,
Proximity to the tracking volume allows lower average tracking error (i.e., error amplification minimized with a small distance to the fiducial markers as compared to, e.g., having markers out side of the bore that are tracked using an external optical device),
Fiducial frame is always underneath the patient and does not interfere with patient positioning, and does not require additional preparation time to set up the markers prior to MR imaging or RT treatment.
Accurate indexing of the patient couch to enable correct patient positioning to ensure that the anatomical region-of-interest is placed over the appropriate patient fiducial frame.
MR/X-ray encoding markers are used to automatically identify each of the fiducial frames for the corresponding anatomy.
High spatial accuracy of the patient couch control systems avoids the need for specific 'localizing' MRI sequences, and ensures consistent positioning for X-ray imaging system mounted on the RT unit.
Placement of MR/X-ray markers in patterns allows identification and localization of the markers when only a subset of markers is captured in the MR and X-ray fields-of-view.
Marker positioning enables accurate mapping of MR coordinate system with either standard 2D projection X-rays as well as cone-beam CT imaging.
The ability to support automatic registration without the need to remove the fiducial frame.
Lower average error since fiducial frame is rigidly embedded into the patient couch top.
The application of MR and X-ray visible markers embedded into the couch top for alignment of RT treatment.
MR/X-ray encoding markers can be used to automatically identify the type of fiducial frame (i.e. head/neck or abdominal)
Placement of MR/X-ray markers in patterns allows identification and localization of the markers when only a subset of markers is captured in the MR and X-ray fields-of-view.
The use of markers that are both MR and X-ray visible that are embedded in the patient couch top for MR guided RT.
One solution is to utilize a movable magnet that can be brought into the RT bunker for imaging and then retracted prior to radiotherapy procedures. This enables RT that is carried out using the currently available devices, and does not require complex design of hybrid systems that are capable of simultaneous MR and RT procedures.

The arrangement described herein also provides a Support Component for MRI guided Radiotherapy. To incorporate a movable MRI into RT requires a modified support system that will allow the patient to be imaged and treated on the same couch, however, this requires that the couch be MRI compatible and have an extended range of motion to reach the MRI when in position for imaging. A critical aspect of this problem is the interaction of the MRI static magnetic field with the patient couch, which employs several electronic motors designed to provide different degrees of motion.

One objective of this invention to provide an improved patient support system for MRI guided RT, using a patient table in which the patient remains on the same table during both MRI and RT steps. In this invention, the couch is able to rotate 180 degrees from the isocentre of linear accelerator for MR imaging procedures, and then rotate back to the RT isocentre for radiation treatment. This will require that the longitudinal range of motion of the patient table is extended to provide a safe distance between the static magnetic field of the magnet and critical positional motors in the patient couch.

The materials in the couch top are both MR compatible and radiolucent to enable both MR and X-ray imaging procedures. The couch top incorporates placeholders for the RF coils required for imaging the head and neck, abdomen and lower pelvic region (prostate, cervix). The couch top also includes the necessary notches at the end of the table to maintain a similar function to standard linear accelerator and CT patient couch tops.

BRIEF DESCRIPTION OF THE DRAWINGS

Embodiments of the invention will now be described in conjunction with the accompanying drawings in which:

FIG. 8 is a flow chart of the automatic registration algorithm.

FIG. 9 is an isometric view of the table top of FIG. 1.

In the drawings like characters of reference indicate corresponding parts in the different figures.

DETAILED DESCRIPTION

In FIGS. 1 to 5 is shown a schematic diagram of the MRI and external beam RT therapy system within the external beam bunker room configuration. This diagram includes a magnet 10, having a bore 10A into which a patient 12 can be received on a patient couch top 15, which is attached to a patient couch 13.

Figure 1:
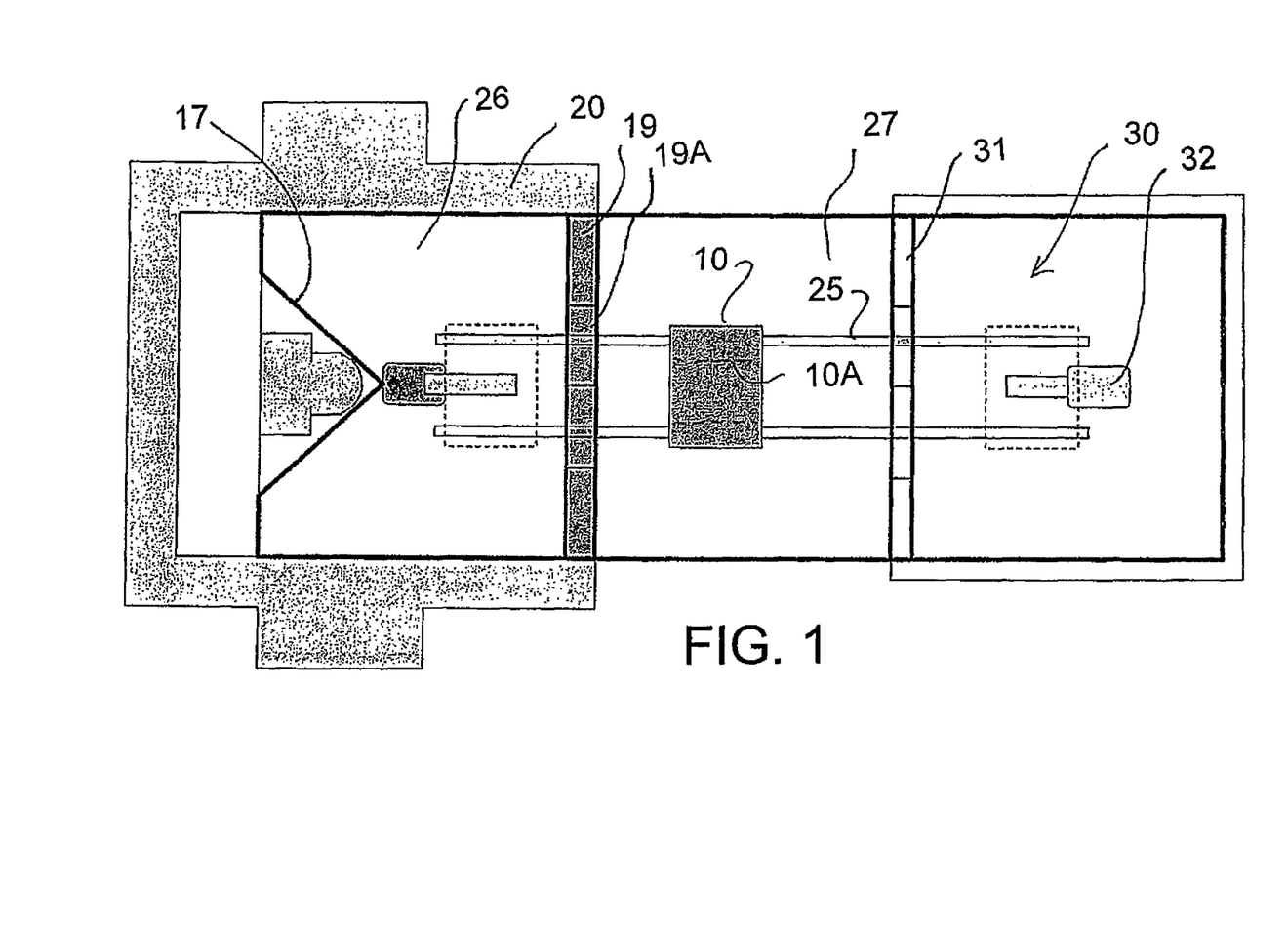
FIG. 1 is a top plan view of an apparatus for radiation treatment of a patient including an MR imaging system showing different positions of the movable magnet.

The movable magnet is carried on a rail system 25 with a support 23 suspended on the rail system. Further details of this construction are available from published US application 2008/0038712 published Feb. 14, 2008 assigned to the present assignees, the disclosure of which is incorporated herein by reference.

A suitable radiation therapy system 4 is available from Varian. This can use different radiation including proton beams, brachytherapy or X-ray. The Varian radiation therapy system is capable of delivering therapeutic radiation to the patient using an x-ray beam formed through a multi-leaf collimator to modulate the intensity of the radiation delivered.

The Varian radiation therapy unit also includes a gantry-mounted x-ray imaging system 4A capable of performing cone-beam CT imaging immediately prior to radiation therapy, which enables image-guided radiotherapy. Alternatively, the Varian radiation therapy system is a device capable of delivering brachytherapy. This system also includes an image-guidance system that consisted of an x-ray imaging system. The disclosure of this material is incorporated herein by reference.

Figure 2:
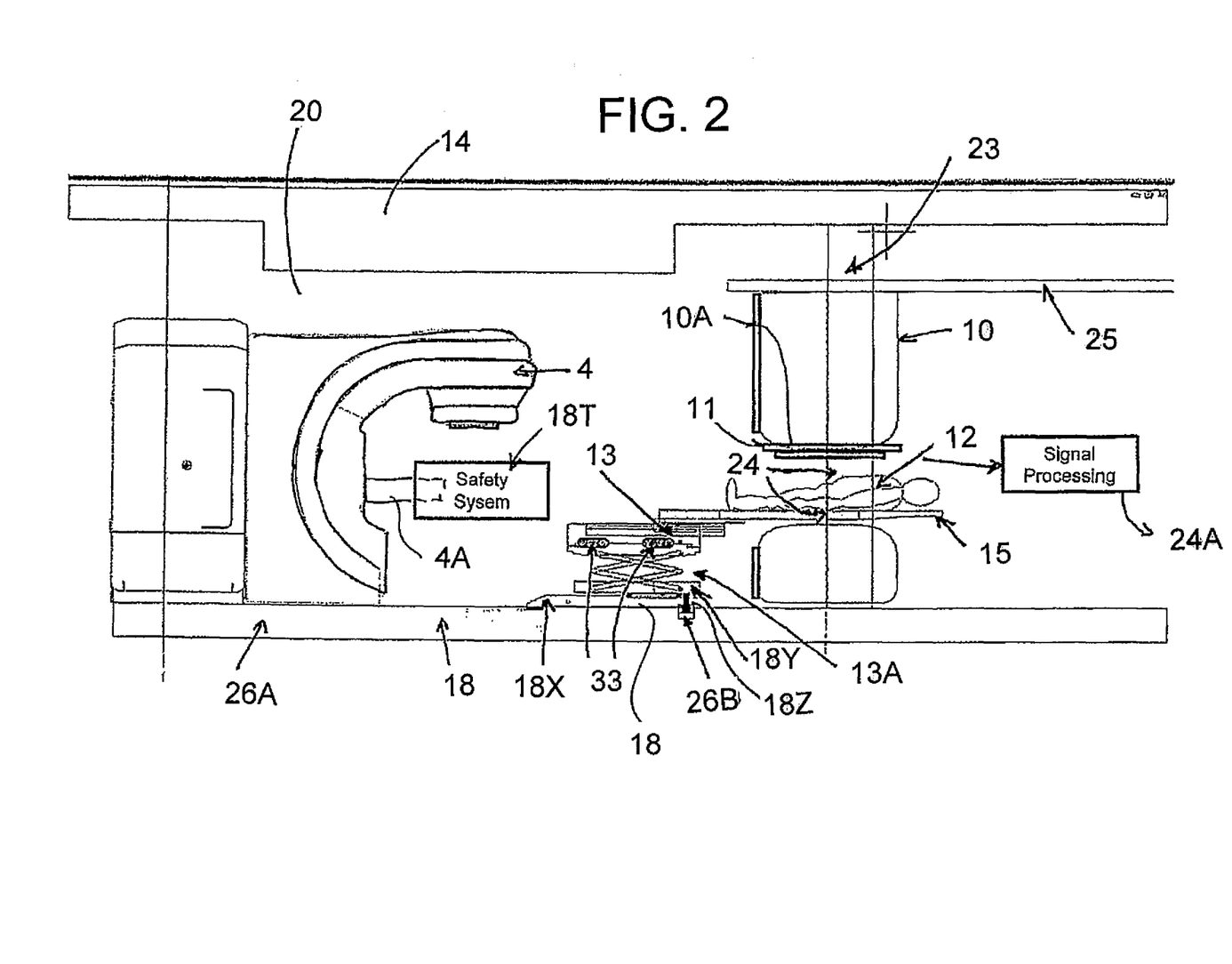
FIG. 2 is a side elevational view of the apparatus of FIG. 1 showing the patient support table cooperating with the magnet in the imaging position and also illustrates the patient support table showing the base, toe portion, heel portion, support wheels, motors and couch or table top.
Figure 3:
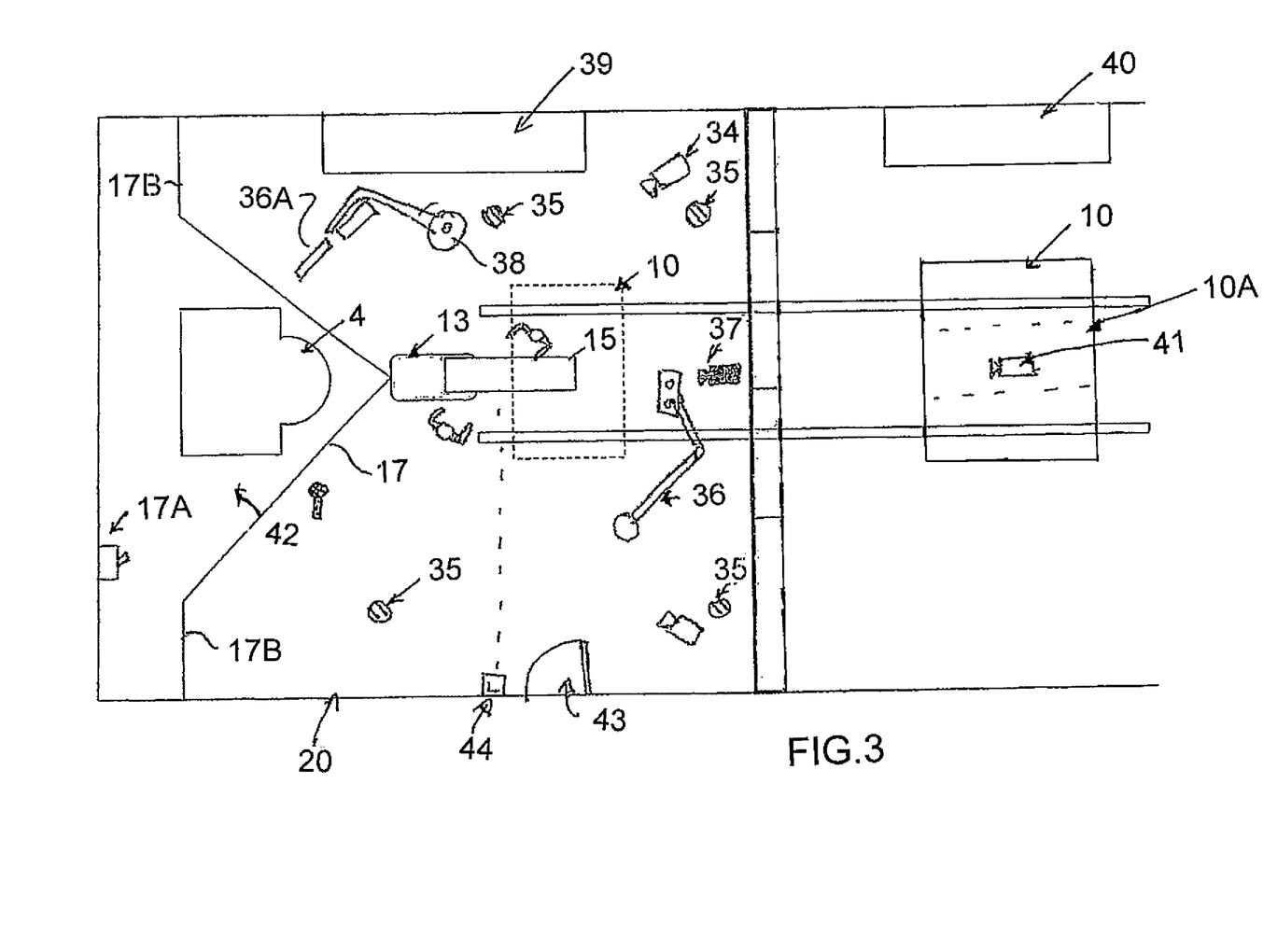
FIG. 3 is a top plan view of the apparatus of FIG. 1 showing the RF shielding doors.

The Patient Handling System or support table is shown in FIG. 3, indicated generally at 13 and 15. The patient support table 13 includes a base or pedestal 13A which allows the base to move a patient support portion 15 to required locations in height and in orientation. At the top of the base 13A is mounted the patient support portion 15 in the form of a generally planar body 15 formed of a fiber reinforced plastics material so as to define a surface area sufficient for supporting the patient while lying on the patient support portion. In FIGS. 1 and 2, the patient and the support structure are rotated 180 degrees from the position of the RT isocentre 16, with the movable MRI in position for imaging. The pedestal 13A is mounted on a turntable 18 for rotation about a vertical axis.

The table can be a multi axis movable or "robot" table of a type also available from Varian. This acts to hold the base stationary while the table top can be moved to any orientation around the base and relative to axes transverse to the base.

As best shown in FIG. 2, the table is shown including the base 18, toe portion 18X, heel portion 18Y, support wheels 18Z, motors 33 and couch or table top 15. There are also provided safety control systems 18T at a suitable location relative to the system and integrated into the operation of the patient support table to prevent movement when in position for MR imaging to mitigate the possibility of collision between the patient support table and the RF-shielded door arrangement.

The patient support table 13 is arranged to rotate 180 degrees from the isocentre of the treatment apparatus for cooperation with the MR magnet in MR imaging procedures, and then rotate back to the isocentre for treatment.

The patient support table 13 employs several electronic motors 33 designed to provide different degrees of motion with the motors and controls therefor arranged to avoid interaction of the MRI static magnetic field.

The longitudinal range of motion of the patient support table is extended to provide a safe distance between the static magnetic field of the magnet and positional motors in the patient support table.

The automated system de-energizes the motors 33 once the patient support table is locked in place for MR imaging, and prevents any unsafe actions once locked into place.

The safety system also guarantees that the patient support table is in the appropriate locked position prior to the magnet moving over the patient.

The materials in the table top 15 of the patient support table are both MR compatible and radiolucent to enable both MR and X-ray imaging procedures.

The table top 15 incorporates placeholders for RF coils 24 required for imaging the head and neck or the thorax, abdomen and/or lower pelvic region.

The table top 15 also includes notches at the end of the table top required to maintain a similar function to standard linear accelerator and CT patient table tops.

The table top 15 uses radiolucent and MRI compatible materials in the table top which allows the patient support table to be used in MRI and X-ray imaging systems without degrading the image quality of either system.

The system further includes a receive coil system generally indicated at 24, which receives MR signals generated from the human body in a conventional manner. An RF control system acts to control the transmit body coil 11 and to receive the signals from the receive coil in the general area of 12. When the imaging procedure is complete, the receive coils are attached to the outside of the magnet for transport back to the diagnostic room.

As shown in FIG. 1, the external beam bunker room 26 is enclosed within walls 20, ceiling 14 and floor 26A comprised of radiation and RF shield material. The external beam RT room 26 is separated from a diagnostic imaging room 27 by a set of radiation and RF shielded bunker doors 19, so as to prevent radiation exposure to subjects in the adjacent diagnostic room during RT treatment delivery. The external beam bunker doors 19 are open during the imaging procedure and closed during RT delivery.

A second set of RF shield doors 17, situated between the RT and MRI system, are used to isolate the RF generating components of the RT from the MRI system. These doors account for the RF shielding requirements across the turntable portion 18 of the patient support table 13. These doors are closed for MRI procedures and opened for RT delivery. An egress switch 17A is included within the RF-shielded doors to enable a manual override, which allows someone trapped behind the RF doors to open the RF doors even in the event of a power outage.

Following the imaging procedures, the RF shield doors 17 are opened, and the MRI system is moved out of the external beam RT room 26. After the MRI is out of the bunker room, the RF-shielded doors 19 between the MRI and RT systems 17 are opened, and the patient 12 is rotated 180 degrees to the RT position using the patient support table 13. The patient alignment is adjusted based on the imaging results, and the RT beam is delivered from the treatment apparatus 4 to the lesion via the conventional collimator and rotating support.

In FIGS. 1 and 2 the three-room configuration is displayed, with the rooms for external beam treatment 26, diagnostic imaging 27 and brachytherapy 30. RF and radiation-shielded doors 31 are placed between the diagnostic room 27 and brachytherapy bunker 30. The patient is positioned on the brachytherapy support table 32, which can allow the MRI system to move over the patient, and also has the necessary patient supports for brachytherapy procedures.

FIG. 3 provides a sketch of the complete room configuration for the three-room configuration with brachytherapy. In addition to the previous figures, components such as the two patient cameras 34, MR-compatible pot lights 35, IR tracking camera system 36 are positioned within the system room configuration. Based on the radiation damage that could be incurred at certain points in the room design, the third patient camera 37 is a radiation hardened camera that has electrical components not seriously affected by radiation exposure. The egress switch 17A is also included in FIG. 3. LCD monitors 36A are positioned at approximately position 38 to be easily visible by the clinical staff in the room. The bunker room also includes cabinets 39 for storage of immobilization and other radiotherapy devices. The MR coils used in the imaging procedures are located in the diagnostic room storage cabinets 40. To enable continuous patient monitoring, an MR-compatible camera 41 is mounted inside the bore 10A of the movable MRI system 10. Speakers and a microphone are installed at approximately position 42, which enable continuous communication with the patient when the clinical staff are outside of the room. A personnel access sliding door 43 is designed into the room to provide direct access to the bunker room. The room also has a laser system 44 mounted on the bunker room wall 20, that allows the clinical staff to accurately position the patient prior to MR imaging or radiation therapy delivery.

The apparatus for radiation therapy of a patient therefore includes the patient support table 13, a magnetic resonance imaging system for acquiring MR images of an imaging volume including the target location of the patient and the radiation treatment apparatus 4.

The MR imaging system includes the MR magnet 10 with gradient coil 10A operable to generate a variable magnetic field to be applied to the patient, the magnet having a cylindrical bore 10A for surrounding the target location of the patient. The imaging system further includes the RF transmit coil arrangement 11 for generating an RF pulse in a transmit stage to be applied to the subject to be imaged such that the subject generates an MR signal in response to the magnetic field and the RF pulse applied. The signal is picked up by the receive coil arrangement 24 for acquiring the MR signal in a receive stage. The received signal is transmitted to a signal processing system 24A for receiving the MR signal for carrying out signal processing by which an image is generated.

The beam or brachytherapy treatment apparatus 4 is arranged for applying a radiation therapy to a target location in the patient on the support table.

The patient support table 15 and the treatment apparatus 4 are mounted in a treatment room having an opening 19A which includes a radiation shielded door arrangement 19 defined by two doors movable at right angles to the walls to a center closed position operable to close the opening 19A.

The MR magnet 10 is mounted for movement from a position exterior of the radiation shielded door arrangement 19 into or through the opening 19A to an imaging position for cooperation with the patient on the patient support table 15 for MR imaging.

The RT system 4 is separated from the magnet during imaging by the RF-shielded door arrangement 17 in the treatment room arranged to be movable between a closed position, separating at least part of the treatment apparatus from the magnet when in the imaging position, and an open position in which the treatment apparatus is accessible to the patient on the patient support table for radiation therapy.

The RF-shielded door arrangement 17 is arranged in the closed position to isolate RF noise critical electronic components of the treatment apparatus 4 from the magnet 10 and receive coil arrangement 24 while allowing the critical electronic components of the treatment apparatus 4 to remain active without shutdown. This is necessary to avoid unacceptable delays which would be caused by a shut down of the system and restarting.

Figure 4:
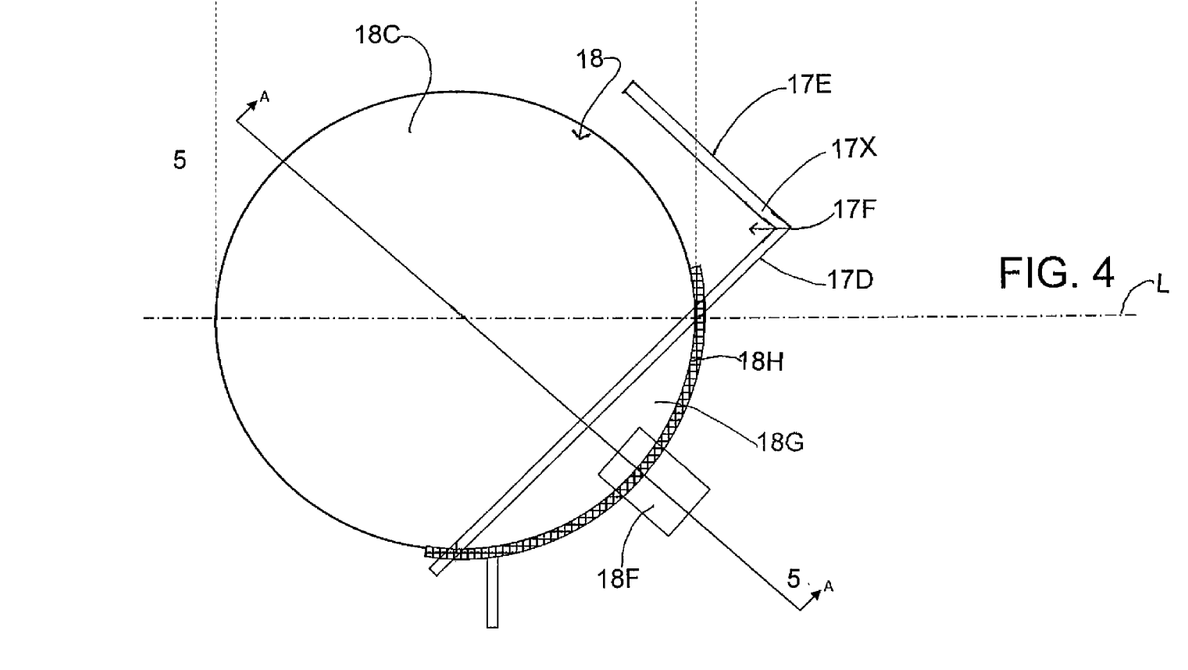
FIG. 4 is a top plan view of the apparatus of FIG. 1 showing the RF shielding doors cooperating with a turntable of the patient support table.
Figure 5:
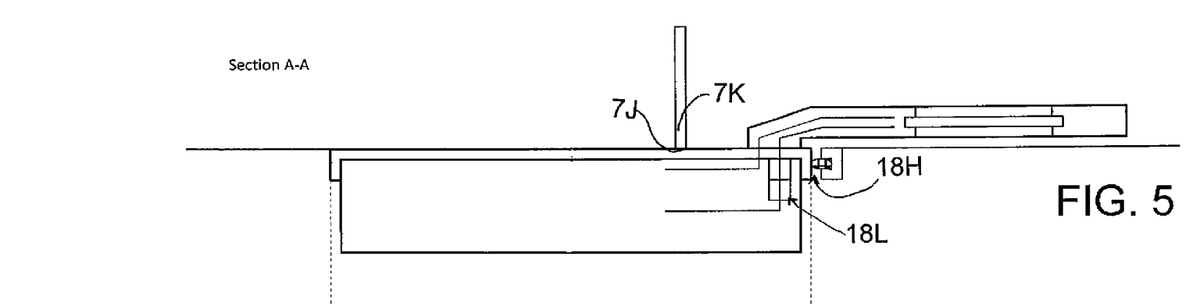
FIG. 5 is a cross-sectional view along the lines A-A of FIG. 4 showing the RF shielding doors.

The RF-shielded door arrangement 17 includes a suitable conductive layer typically formed of copper which halts and RF signals at the conductor. As shown in FIGS. 3 and 4, the RF-shielded door arrangement includes doors or components 17 which together span the treatment room and which extend at an inclined angle to the patient support table. Thus there is provided an RF shielded wall portion 17B arranged on each side of the treatment apparatus at an angle to a longitudinal axis of the patient support table which can remain fixed and in position partly spanning the room. Each wall portion 17B cooperates with a respective RF shielded door 17 which can move across the treatment room along its respective wall portion from the inner edge of the respective wall portion so that the doors meet at the middle and form a continuous RF conductive shield. The position of the wall portions 17B is such that the table can rotate around the vertical central axis to take up its two positions while moving inside the inner edges 17C of the wall portions.

As best shown in FIG. 4, the doors 17D and 17E meet at a point 17F which is symmetrical to the center line L of the system, and both doors extend across the turntable 18. Thus the RF-shielded door 17D extends across a part 18 of the base so as to exclude the main part 18C of the base from the area containing the MR magnet. A portion of the base 18 as indicated at 18G is arranged inside the area of the magnet with the toe portion of the couch.

Thus the RF-shielding door arrangement 17 includes a RF-shielding inflatable bladder 7J in a bottom edge 7K of the doors that maintains RF-shielding across the base 18 of the patient support table. The surface baseplate of the turntable 18 is formed of a conductive material and there is provided a movable contactor 18H in the form of an inflatable bladder connected to the RF shield for engaging the turntable. In this way the continuous conductive shield communicates through the turntable 18C and the door 17D, mounting the parts of the table which are inside the zone of the magnet so that they are all shielded from the RF signals generated by the quiescent but active treatment system in the zone behind the doors 17.

The two parts 17D, 17E of the doors come together at an apex and are inclined to a longitudinal axis of the room so as to enclose the treatment system 4 on the left of the doors within the triangular shape defined by the two doors.

Cables for providing control signals to the patient support table pass through a gland at the part of the RF shield defined by the portion 18G of the turntable. In order to ensure that signals generated in the cables by the RF fields within the magnet zone are not communicated through to the zone of the treatment apparatus and vice versa, an RF filter system 18L is connected in the cables to filter the signals.

On the patient support table some of the control elements are operated by fiber optic cables 18M which pass through the RF shield at the base portion 18G.

There are provided one of more detectors 17X on the RF-shielded door arrangement to prevent the door arrangement from closing to the position 17F if there is an object within the path of movement.

In one arrangement, there are provided three rooms including a first room for the Radiation treatment system 26, a third room 30 for the brachytherapy system combined with a second intermediate diagnostic room 27 in the middle to provide a three-room solution that provides image-guidance for both external beam and brachytherapy RT procedures using the same movable MRI magnet.

In FIGS. 1 and 2 there are provided two separate rooms where the first is a radiation-shielded "bunker" that houses the treatment apparatus and the second room houses the MR magnet for basic diagnostic procedures.

Figure 6:
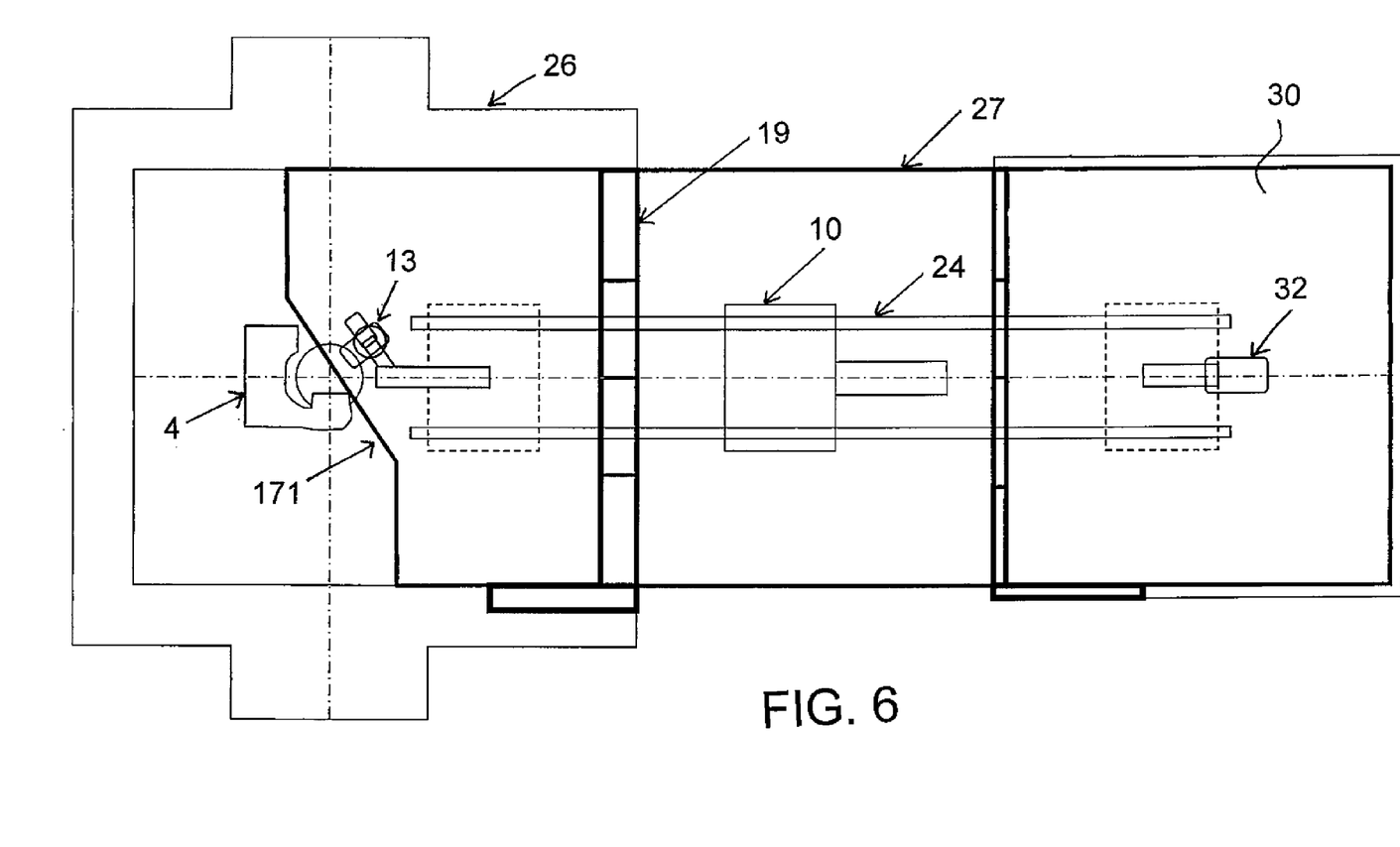
FIG. 6 is a top plan view of an apparatus using the arrangement of FIG. 1 in an alternative configuration of the rooms.
Figure 7:
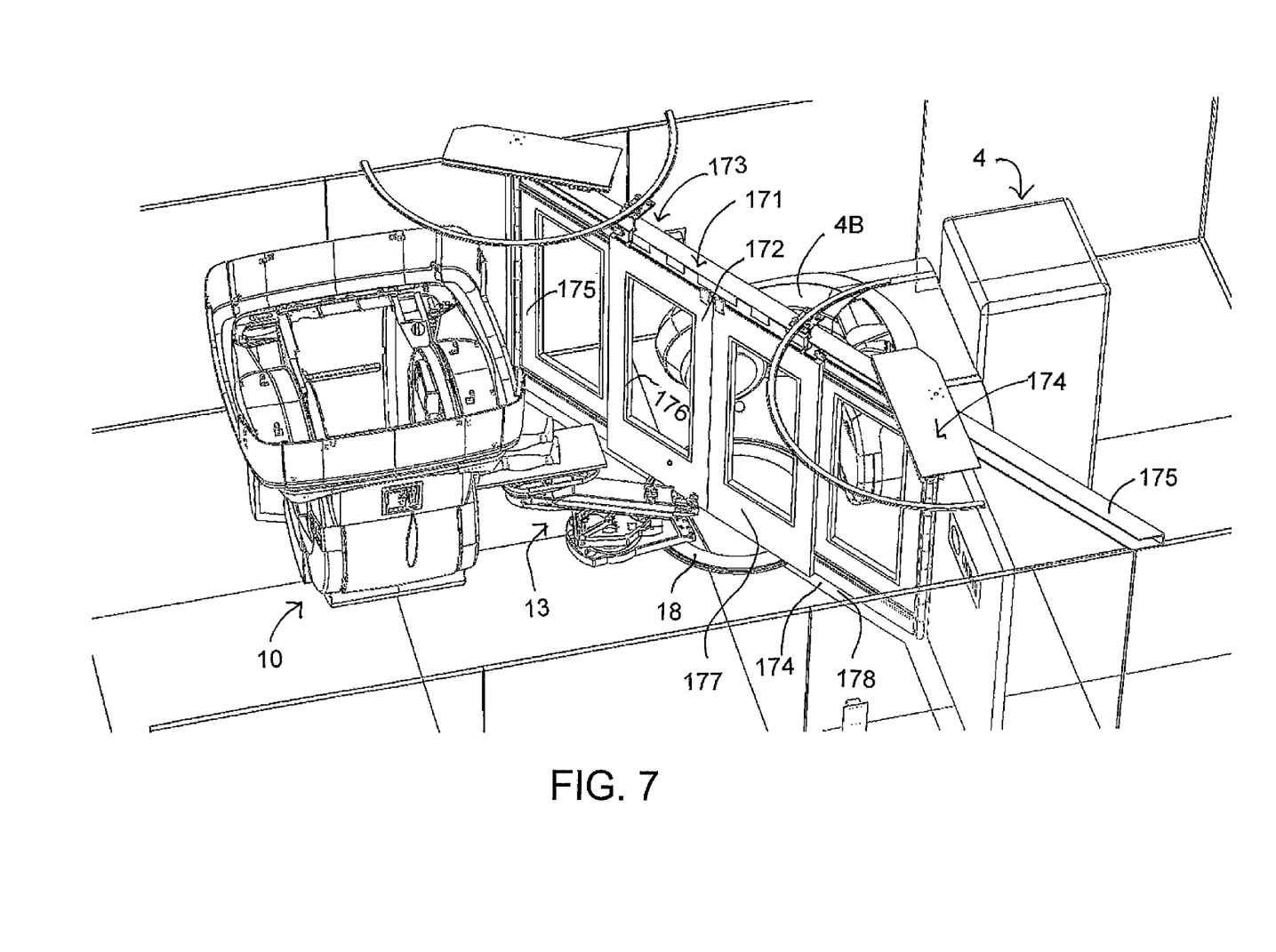
FIG. 7 is an isometric view of the embodiment of FIG. 6 showing the RF shielding doors in the closed position for operation of the MR Imaging system.
Figure 8:
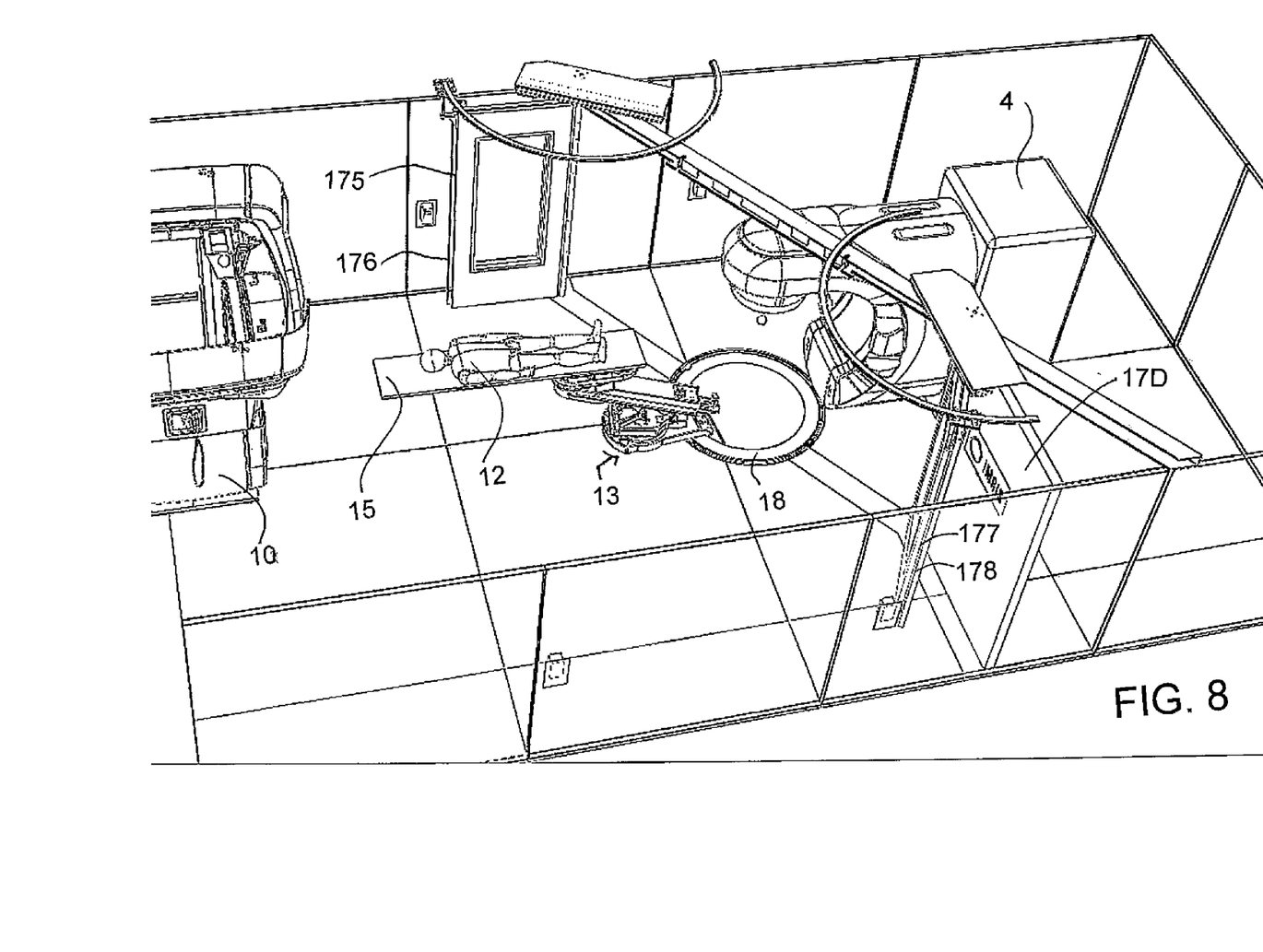
FIG. 8 is an isometric view of the embodiment of FIG. 6 showing the RF shielding doors in the open position with the magnet moved partly away for operation of the Radiation treatment system.

Turning now to FIGS. 6, 7 and 8, substantially the same arrangement as that of FIGS. 1 and 2 is shown. In this arrangement the robotic table 13 available from Varian which rotates around the turntable 18 is shown in more detail.

In this arrangement the RF shielding door arrangement indicated generally at 171 is different in that it includes a part 172 extending fully across the turntable 18 to a position 173, 174 on either side of the turntable 18. The treatment apparatus 4 includes a head 4B rotatable about an axis longitudinal of the treatment room.

The head 4B, as is well known in these systems rotates around the longitudinal axis to direct the radiation to the treatment location from different angles around the patient.

In this arrangement use is made of the position of the head where the head 4B is turned 90 degrees to one side of the patient support table. This enables the door part 172 to pass generally diagonally across the turntable 18 with the head on the side of the door 172 remote from the magnet. The door 172 is formed of a conductive material to create the required RF shield. The bottom of the door cooperates with a band 174 of conductive material across the floor and similarly the top of the door 1'72 cooperates with a band 175 across the ceiling. Using a bi-fold or sliding door arrangements made up of door panels 175, 176, 1'77 and 178 allows the door arrangement to fold back against the wall on one side and against a wall portion 17D on the other side. In this way the door arrangement can be moved to both positions without difficulty, without interfering with the patient on the table 13, while leaving the patient and table 13 wholly exposed for the magnet 10 as shown in FIG. 7 and while leaving the area open as shown in FIG. 8 for the treatment process.

Figure 9:
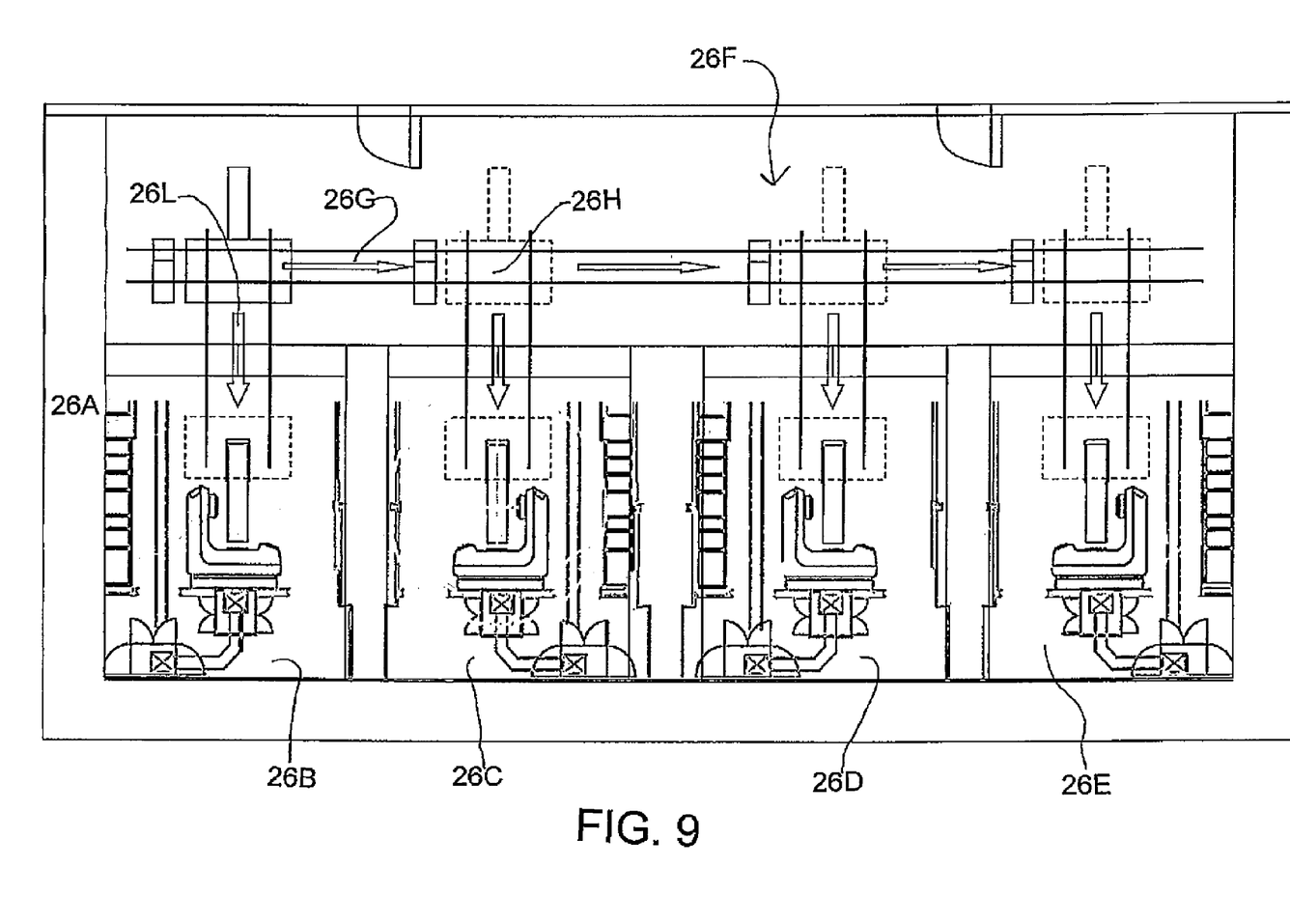
FIG. 9 is a top plan view of an apparatus using the arrangement of FIG. 1 in a further alternative configuration of the rooms.

Turning now to the separate embodiment shown in FIG. 9, the room configuration includes a row 26A of rooms 26B to 26E each having a respective treatment apparatus, a respective patient support table and a respective radiation shielded door arrangement and the magnet is arranged to move along a path or passageway 26F outside the row of radiation shielded door arrangements. From this path, the magnet is arranged to move linearly along the path 26G outside the row of radiation shielded door arrangements to each room in turn as required. From this position the magnet rotates about a vertical axis 26H at each room to cooperate with the patient support table therein. In addition to the rotation, the magnet may also move in a direction 26L at right angles to the path 26G to enter the opening of the room concerned. However in some arrangements the magnet may not be able to move in the direction 26L and the cooperation between the table and the magnet is achieved by movement of the table alone.

In FIGS. 10A to 10E are shown a number of different embodiments of couch top designed to mount on the Varian robotic table mentioned above.

In each case the table top is manufactured of materials which make it MR compatible and radiolucent so as to allow imaging by the MR system and by the x-ray imaging system 4A of the treatment system 4 without generation of imaging artifacts.

Figure 10A:
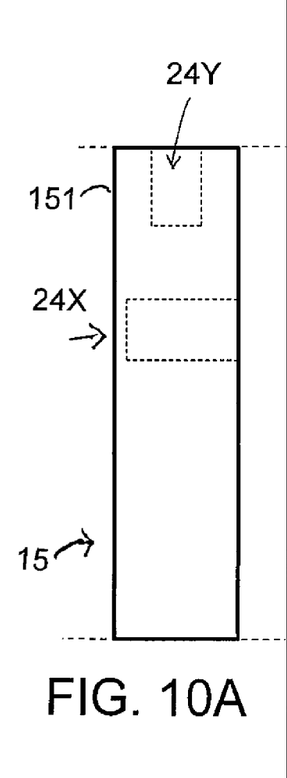
FIGS. 10A to 10E show alternative embodiments of a couch top

In FIG. 10A there is shown a one piece top 15 having a length to receive the whole body of the patient including an end section 151 which underlies the head. A first slot in the thickness of the top is provided at 24X to allow a posterior coil to be inserted at the pelvic region for pelvic imaging. A second slot in the thickness of the top is provided at 24Y to allow a posterior coil to be inserted at the head region 151 for head imaging.

Figure 10B:
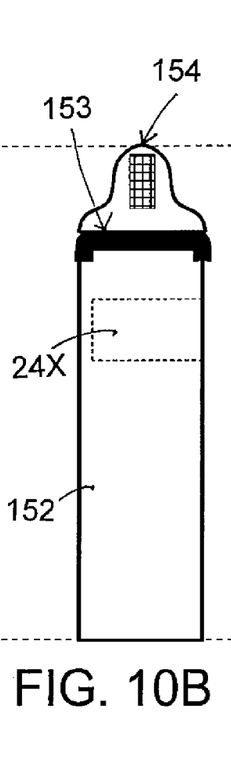
Figure 10C:
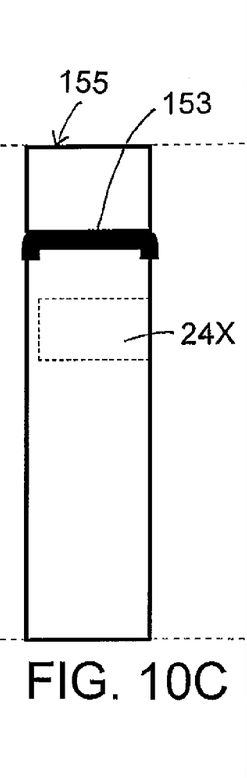

In FIGS. 10B and 10C are shown three piece tops with a base piece 152, a connector piece 153 and a head support piece 154, 155. The connector piece provides connector structures to hold the head piece in place at the end of the base piece. Various designs of connector can be provided. A slot 24 X is provided in the base piece in each arrangement. The head support 155 in FIG. 10C is merely a flat support plate. In FIG. 10B, the head support 154 is provided as a head/neck treatment mode shaped to provide minimum material to reduce the interference with the radiation.

Figure 10D:
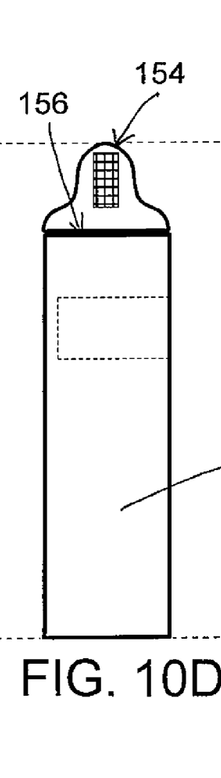
Figure 10E:
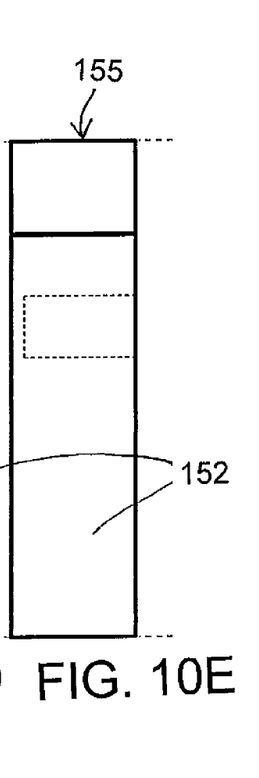

In FIGS. 10D and 10E are shown two piece tops with a base piece 152 and a head support piece 154, 155, where the connector piece 153 is omitted and the connector function defined instead between the base and head sections directly. Various designs of connector can be provided. A slot 24 X is provided in the base piece in each arrangement. The head supports 154 and 155 are as previously described.

The invention claimed is:

1. Apparatus for radiation therapy of a patient comprising:
   a radiation treatment room which is radiation shielded and has an opening which includes a radiation shielded door arrangement operable to close the opening;
   a patient support table;
   a magnetic resonance imaging system to acquire MR images of an imaging volume including a target location of the patient;
   the imaging system including:
      an MR magnet operable to generate a magnetic field to be applied to the patient, wherein the MR magnet has a cylindrical bore to surround the target location of the patient;
      an RF transmit coil arrangement to generate an RF pulse in a transmit stage to be applied to the target location to be imaged such that the target location generates an MR signal in response to the magnetic field and the RF pulse applied;
      a receive coil arrangement to acquire the MR signal in a receive stage;
      and a signal processing system to receive the MR signal for carrying out signal processing by which an image is generated;
   a treatment apparatus to apply a radiation therapy to a target location in the patient on the patient support table;
   the patient support table and the treatment apparatus being mounted in said radiation treatment room;
   the MR magnet being mounted for movement from a position exterior of the radiation shielded door arrangement into the opening to an imaging position for cooperation with the patient on the patient support table for MR imaging;
   the MR magnet being mounted for movement from the imaging position to the exterior position for the radiation treatment of the patient on the patient support table;
   wherein there is provided in the radiation treatment room an arrangement separate from the radiation shielded door arrangement to prevent RF signals from the treatment apparatus from interfering with the magnetic resonance imaging system during imaging at the patient support table;
   and wherein both the patient support table and the treatment apparatus are arranged to remain at a treatment location in the radiation treatment room when the magnet is moved to the imaging position.

2. The apparatus according to claim 1 wherein there is provided an RF-shielded door arrangement in the treatment room arranged to be movable between a closed position, separating at least part of the treatment apparatus from the MR magnet when in the imaging position, and an open position in which the treatment apparatus is accessible to the patient on the patient support table for radiation therapy, the RF-shielded door arrangement being arranged in the closed position to isolate RF noise critical electronic components of the treatment apparatus from the magnet and receive coil arrangement while allowing the critical electronic components to remain active without shutdown.

3. The apparatus according to claim 2 wherein the patient support table comprises a patient support couch cantilevered on a support base which includes a turntable formed of a conductive material for rotation about a vertical axis and wherein the RF-shielded door arrangement includes at least a part which extends across the turntable so as to exclude the part of the turntable from the MR magnet.

4. The apparatus according to claim 3 wherein said at least a part of the RF shielded door arrangement extends across the turntable at an angle inclined to a longitudinal axis of the cylindrical bore of the MR magnet.

5. The apparatus according to claim 3 wherein the RF shielded door arrangement includes a portion arranged on each side of the treatment apparatus at right angles to the longitudinal axis.

6. The apparatus according to claim 3 wherein the RF-shielded door arrangement includes a first part extending partly across the turntable and a second part extending partly across the turntable where the parts meet at an apex to enclose the treatment apparatus.

7. The apparatus according to claim 3 wherein the RF-shielded door arrangement includes a part extending fully across the turntable to a position on either side of the turntable where the treatment apparatus includes a head rotatable about an axis longitudinal of the treatment room and wherein the head is turned to a position at one side of the patient support table to enable the part to pass across the turntable with the head on a side of the part remote from the MR magnet.

8. The apparatus according to claim 1 wherein cables to provide control signals to the patient support table pass through an RF shield and include an RF filter.

9. The apparatus according to claim 1 wherein the patient support table includes control elements operated by fiber optic cables which pass through an RF shield.

10. The apparatus according to claim 1 wherein there are provided at least three rooms in a row including said Radiation treatment room which is used for external beam treatment, a third room for a brachytherapy system spaced from the Radiation treatment room and a second diagnostic room intermediate the radiation treatment room and the third room with the magnet being movable into each of said at least three rooms to provide image-guidance for both the external beam and brachytherapy RT procedures using the same movable MRI magnet.

11. The apparatus according to claim 1 wherein there are provided at least three rooms in a row at least one of which comprises said Radiation treatment room and wherein the magnet is arranged to move linearly along a path outside the row of rooms and to rotate at each room to cooperate with a patient support table therein.

12. The apparatus according to claim 1 wherein the patient support table is arranged to rotate 180 degrees from the isocenter of the treatment apparatus for cooperation with the MR magnet in MR imaging procedures, and then rotate back to the isocenter for treatment.

13. The apparatus according to claim 1 wherein the patient support table employs a plurality of electronic motors designed to provide different degrees of motion with said plurality of motors and controls therefor arranged to avoid interaction with said magnetic field.

14. The apparatus according to claim 1 wherein an automated safety system de-energizes motors of the patient support table when the patient support table is locked in place for MR imaging, and prevents any unsafe actions once locked into place.

15. The apparatus according to claim 14 wherein said automated safety system also guarantees that the patient support table is in the appropriate locked position prior to the MR magnet moving over the patient.

* * * * *